United States Patent
Dowling et al.

(10) Patent No.: US 7,042,172 B2
(45) Date of Patent: May 9, 2006

(54) SYSTEMS AND METHODS FOR PROVIDING ILLUMINATION IN MACHINE VISION SYSTEMS

(75) Inventors: Kevin J. Dowling, Westford, MA (US); George G. Mueller, Boston, MA (US); Ihor A. Lys, Boston, MA (US)

(73) Assignee: Color Kinetics Incorporated, Boston, MA (US)

( * ) Notice: Subject to any disclaimer, the term of this patent is extended or adjusted under 35 U.S.C. 154(b) by 0 days.

(21) Appl. No.: 10/664,415

(22) Filed: Sep. 17, 2003

(65) Prior Publication Data

US 2004/0113568 A1    Jun. 17, 2004

Related U.S. Application Data

(63) Continuation of application No. 09/944,523, filed on Aug. 31, 2001, now Pat. No. 6,624,597.

(60) Provisional application No. 60/229,849, filed on Sep. 1, 2000.

(51) Int. Cl.
*G05F 1/00* (2006.01)

(52) U.S. Cl. .................. 315/294; 315/312; 315/318; 250/227.29; 362/231

(58) Field of Classification Search ........ 315/312, 315/360, 362, 291, 292, 297, 300, 302, 307, 315/76, 318, 294; 250/227.29, 578.1, 234; 362/496, 231, 259, 554, 580, 800
See application file for complete search history.

(56) References Cited

U.S. PATENT DOCUMENTS

| | | | |
|---|---|---|---|
| 2,909,097 A | 10/1959 | Alden et al. | |
| 3,318,185 A | 5/1967 | Kott | |
| 3,561,719 A | 2/1971 | Grindle | |
| 3,586,936 A | 6/1971 | McLeroy | |
| 3,601,621 A | 8/1971 | Ritchie | |
| 3,643,088 A | 2/1972 | Osteen et al. | |
| 3,746,918 A | 7/1973 | Drucker et al. | |
| 3,818,216 A | 6/1974 | Larraburu | |
| 3,832,503 A | 8/1974 | Crane | |
| 3,858,086 A | 12/1974 | Anderson et al. | |
| 3,909,670 A | 9/1975 | Wakamatsu et al. | |
| 3,924,120 A | 12/1975 | Cox, III | |
| 3,958,885 A | 5/1976 | Stockinger et al. | |
| 3,974,637 A | 8/1976 | Bergey et al. | |
| 4,001,571 A | 1/1977 | Martin | |
| 4,054,814 A | 10/1977 | Fegley et al. | |

(Continued)

FOREIGN PATENT DOCUMENTS

AU    6 267 9    12/1996

(Continued)

OTHER PUBLICATIONS

"LM117/LM317A/LM317 3-Terminal Adjustable Regulator", National Semiconductor Corporation, May 1997, pp. 1-20.

(Continued)

*Primary Examiner*—Haissa Philogene
(74) *Attorney, Agent, or Firm*—Foley Hoag LLP

(57) ABSTRACT

A lighting system associated with a machine vision system. The machine vision system may direct lighting control commands to the lighting system to change the illumination conditions provided to an object. A vision system may also be provided and associated with the machine vision system such that the vision system views and captures an image(s) of the object when lit by the lighting system. The machine vision system may direct the lighting system to change the illumination conditions and then capture the image.

34 Claims, 4 Drawing Sheets

U.S. PATENT DOCUMENTS

| | | |
|---|---|---|
| 4,082,395 A | 4/1978 | Donato et al. |
| 4,096,349 A | 6/1978 | Donato |
| 4,241,295 A | 12/1980 | Williams, Jr. |
| 4,272,689 A | 6/1981 | Crosby et al. |
| 4,273,999 A | 6/1981 | Pierpoint |
| 4,298,869 A | 11/1981 | Okuno |
| 4,329,625 A | 5/1982 | Nishizawa et al. |
| 4,367,464 A | 1/1983 | Kurahashi et al. |
| 4,388,567 A | 6/1983 | Yamazaki et al. |
| 4,388,589 A | 6/1983 | Molldrem, Jr. |
| 4,392,187 A | 7/1983 | Bornhorst |
| 4,420,711 A | 12/1983 | Takahashi et al. |
| 4,500,796 A | 2/1985 | Quin |
| 4,622,881 A | 11/1986 | Rand |
| 4,625,152 A | 11/1986 | Nakai |
| 4,635,052 A | 1/1987 | Aoike et al. |
| 4,647,217 A | 3/1987 | Havel |
| 4,656,398 A | 4/1987 | Michael et al. |
| 4,668,895 A | 5/1987 | Schneiter |
| 4,682,079 A | 7/1987 | Sanders et al. |
| 4,686,425 A | 8/1987 | Havel |
| 4,687,340 A | 8/1987 | Havel |
| 4,688,154 A | 8/1987 | Nilssen |
| 4,688,869 A | 8/1987 | Kelly |
| 4,695,769 A | 9/1987 | Schweickardt |
| 4,701,669 A | 10/1987 | Head et al. |
| 4,705,406 A | 11/1987 | Havel |
| 4,706,168 A | 11/1987 | Weisner |
| 4,707,141 A | 11/1987 | Havel |
| 4,727,289 A | 2/1988 | Uchida |
| 4,740,882 A | 4/1988 | Miller |
| 4,753,148 A | 6/1988 | Johnson |
| 4,771,274 A | 9/1988 | Havel |
| 4,780,621 A | 10/1988 | Bartleucci et al. |
| 4,818,072 A | 4/1989 | Mohebban |
| 4,837,565 A | 6/1989 | White |
| 4,843,627 A | 6/1989 | Stebbins |
| 4,845,481 A | 7/1989 | Havel |
| 4,845,745 A | 7/1989 | Havel |
| 4,863,223 A | 9/1989 | Weissenbach et al. |
| 4,874,320 A | 10/1989 | Freed et al. |
| 4,887,074 A | 12/1989 | Simon et al. |
| 4,922,154 A | 5/1990 | Cacoub |
| 4,934,852 A | 6/1990 | Havel |
| 4,962,687 A | 10/1990 | Belliveau et al. |
| 4,965,561 A | 10/1990 | Havel |
| 4,973,835 A | 11/1990 | Kurosu et al. |
| 4,979,081 A | 12/1990 | Leach et al. |
| 4,980,806 A | 12/1990 | Taylor et al. |
| 4,992,704 A | 2/1991 | Stinson |
| 5,003,227 A | 3/1991 | Nilssen |
| 5,008,595 A | 4/1991 | Kazar |
| 5,010,459 A | 4/1991 | Taylor et al. |
| 5,027,262 A | 6/1991 | Freed |
| 5,034,807 A | 7/1991 | Von Kohorn |
| 5,060,065 A | 10/1991 | Wasserman |
| 5,072,216 A | 12/1991 | Grange |
| 5,078,039 A | 1/1992 | Tulk et al. |
| 5,083,063 A | 1/1992 | Brooks |
| 5,095,204 A * | 3/1992 | Novini .................... 250/223 B |
| 5,126,634 A | 6/1992 | Johnson |
| 5,128,595 A | 7/1992 | Hara |
| 5,134,387 A | 7/1992 | Smith et al. |
| 5,142,199 A | 8/1992 | Elwell |
| 5,154,641 A | 10/1992 | McLaughlin |
| 5,164,715 A | 11/1992 | Kashiwabara et al. |
| 5,166,985 A | 11/1992 | Takagi et al. |
| 5,184,114 A | 2/1993 | Brown |
| 5,194,854 A | 3/1993 | Havel |
| 5,209,560 A | 5/1993 | Taylor et al. |
| 5,225,765 A | 7/1993 | Callahan et al. |
| 5,226,723 A | 7/1993 | Chen |
| 5,254,910 A | 10/1993 | Yang |
| 5,256,948 A | 10/1993 | Boldin et al. |
| 5,282,121 A | 1/1994 | Bornhorst et al. |
| 5,294,865 A | 3/1994 | Haraden |
| 5,300,788 A * | 4/1994 | Fan et al. ...................... 257/13 |
| 5,307,295 A | 4/1994 | Taylor et al. |
| 5,329,431 A | 7/1994 | Taylor et al. |
| 5,350,977 A | 9/1994 | Hamamoto et al. |
| 5,357,170 A | 10/1994 | Luchaco et al. |
| 5,365,084 A * | 11/1994 | Cochran et al. ........ 250/559.02 |
| 5,369,492 A | 11/1994 | Sugawara |
| 5,371,618 A | 12/1994 | Tai et al. |
| 5,374,876 A | 12/1994 | Horibata et al. |
| 5,388,357 A | 2/1995 | Malita |
| 5,402,702 A | 4/1995 | Hata |
| 5,404,282 A | 4/1995 | Klinke et al. |
| 5,406,176 A | 4/1995 | Sugden |
| 5,410,328 A | 4/1995 | Yoksza et al. |
| 5,412,284 A | 5/1995 | Moore et al. |
| 5,412,552 A | 5/1995 | Fernandes |
| 5,420,482 A | 5/1995 | Phares |
| 5,421,059 A | 6/1995 | Leffers, Jr. |
| 5,432,408 A | 7/1995 | Matsuda et al. |
| 5,436,535 A | 7/1995 | Yang |
| 5,461,188 A | 10/1995 | Drago et al. |
| 5,463,280 A | 10/1995 | Johnson |
| 5,465,144 A | 11/1995 | Parker et al. |
| 5,489,827 A | 2/1996 | Xia |
| 5,491,402 A | 2/1996 | Small |
| 5,504,395 A | 4/1996 | Johnson et al. |
| 5,519,496 A | 5/1996 | Borgert et al. |
| 5,545,950 A | 8/1996 | Cho |
| 5,561,346 A | 10/1996 | Byrne |
| 5,575,459 A | 11/1996 | Anderson |
| 5,575,554 A | 11/1996 | Guritz |
| 5,592,051 A | 1/1997 | Korkala |
| 5,640,061 A | 6/1997 | Bornhorst et al. |
| 5,642,129 A | 6/1997 | Zavracky et al. |
| 5,673,059 A | 9/1997 | Zavracky et al. |
| 5,701,058 A | 12/1997 | Roth |
| 5,721,471 A | 2/1998 | Begemann et al. |
| 5,734,590 A | 3/1998 | Tebbe |
| 5,751,118 A | 5/1998 | Mortimer |
| 5,752,766 A | 5/1998 | Bailey et al. |
| 5,758,942 A | 6/1998 | Fogal et al. .................. 362/12 |
| 5,769,527 A | 6/1998 | Taylor et al. |
| 5,803,579 A | 9/1998 | Turnbull et al. |
| 5,808,689 A | 9/1998 | Small |
| 5,821,695 A | 10/1998 | Vilanilam et al. |
| 5,848,837 A | 12/1998 | Gustafson |
| 5,850,126 A | 12/1998 | Kanbar |
| 5,851,063 A | 12/1998 | Doughty et al. |
| 5,852,658 A | 12/1998 | Knight et al. |
| RE36,030 E | 1/1999 | Nadeau |
| 5,859,508 A | 1/1999 | Ge et al. |
| 5,896,010 A | 4/1999 | Mikolajczak et al. |
| 5,912,653 A | 6/1999 | Fitch |
| 5,924,784 A | 7/1999 | Chliwnyj et al. |
| 5,946,209 A | 8/1999 | Eckel et al. |
| 5,952,680 A | 9/1999 | Strite |
| 5,959,547 A | 9/1999 | Tubel et al. |
| 5,963,185 A | 10/1999 | Havel |
| 5,974,553 A | 10/1999 | Gandar |
| 5,986,414 A | 11/1999 | Bocchicchio et al. |
| 6,008,783 A | 12/1999 | Kitagawa et al. |
| 6,016,038 A | 1/2000 | Mueller et al. |
| 6,018,237 A | 1/2000 | Havel |
| 6,025,550 A | 2/2000 | Kato |
| 6,031,343 A | 2/2000 | Recknagel et al. |
| 6,068,383 A | 5/2000 | Robertson et al. |
| 6,072,280 A | 6/2000 | Allen |
| 6,095,661 A | 8/2000 | Lebens et al. |

| | | |
|---|---|---|
| 6,097,352 A | 8/2000 | Zavracky et al. |
| 6,132,072 A | 10/2000 | Turnbull et al. |
| 6,135,604 A | 10/2000 | Lin |
| 6,150,774 A | 11/2000 | Mueller et al. |
| 6,166,496 A | 12/2000 | Lys et al. |
| 6,183,086 B1 | 2/2001 | Neubert |
| 6,184,628 B1 | 2/2001 | Ruthenberg |
| 6,196,471 B1 | 3/2001 | Ruthenberg |
| 6,211,626 B1 | 4/2001 | Lys et al. |
| 6,215,409 B1 | 4/2001 | Blach |
| 6,250,774 B1 | 6/2001 | Begemann et al. |
| 6,273,338 B1 | 8/2001 | White |
| 6,292,901 B1 | 9/2001 | Lys et al. |
| 6,340,868 B1 | 1/2002 | Lys et al. |
| 6,459,919 B1 | 10/2002 | Lys et al. |
| 2001/0033488 A1 | 10/2001 | Chliwnyj et al. |

FOREIGN PATENT DOCUMENTS

| | | |
|---|---|---|
| CA | 2 178 432 | 12/1996 |
| EP | 0443289 | 8/1991 |
| EP | 0452905 A1 | 10/1991 |
| EP | 0495305 A2 | 7/1992 |
| EP | 0534710 B1 | 1/1996 |
| EP | 0752632 A2 | 1/1997 |
| EP | 0752632 A3 | 8/1997 |
| EP | 0823812 A2 | 2/1998 |
| EP | 0935234 A1 | 8/1999 |
| EP | 0942631 A2 | 9/1999 |
| EP | 1020352 A2 | 7/2000 |
| EP | 1113215 A2 | 7/2001 |
| FR | 88 17359 | 12/1998 |
| GB | 2045098 A | 10/1980 |
| GB | 2135536 A | 8/1984 |
| GB | 2176042 A | 12/1986 |
| JP | 06043830 | 2/1994 |
| JP | 7-39120 | 7/1995 |
| JP | 8-106264 | 4/1996 |
| JP | 9 320766 | 12/1997 |
| WO | WO 89/05086 | 6/1989 |
| WO | WO 94/18809 | 8/1994 |
| WO | WO 95/13498 | 5/1995 |
| WO | WO 96/41098 | 12/1996 |

OTHER PUBLICATIONS

"DS96177 RS-485 / RS-422 Differential Bus Repeater", National Semiconductor Corporation, Feb. 1996, pp. 1-8.

"DS2003 / DA9667 / DS2004 High Current / Voltage Darlington Drivers", National Semiconductor Corporation, Dec. 1995, pp. 1-8.

"LM140A / LM140 / LM340A / LM7800C Series 3—Terminal Positive Regulators", National Semiconductor Corporation, Jan. 1995, pp. 1-14.

High End Systems, Inc., Trackspot User Manual, Aug. 1997, Excerpts (Cover, Title page, pp. ii through iii and 2-13 through 2-14).

Artistic License, AL4000 DMX512 Processors, Revision 3.4, Jun. 2000, Excerpts (Cover, pp. 7,92 through 102).

Artistic License, Miscellaneous Drawings (3 sheets) Jan. 12, 1995.

Artistic License, Miscellaneous Documents (2 sheets Feb. 1995 and Apr. 1996).

Newnes's Dictionary of Electronics, Fourth Edition, S.W. Amos, et al., Preface to First Edition, pp. 278-279.

"http://www.luminus.cx/projects/chaser", (Nov. 13, 2000), pp. 1-16.

* cited by examiner

SYSTEMS AND METHODS FOR PROVIDING ILLUMINATION IN MACHINE VISION SYSTEMS

CROSS-REFERENCES TO RELATED APPLICATIONS

This Application claims the benefit, under 35 U.S.C. §120, as a continuation (CON) of U.S. Non-provisional application Ser. No. 09/944,523, filed Aug. 31, 2001 now U.S. Pat. No. 6,624,597, entitled "Systems and Methods for Providing Illumination in Machine Vision Systems," which application in turn claims priority to U.S. Provisional Application Serial No. 60/229,849, filed Sep. 1, 2000, entitled "Machine Vision." Each of the foregoing applications is hereby incorporated herein by reference.

BACKGROUND OF THE INVENTION

1. Field of the Invention

The invention relates to machine vision systems. More particularly, this invention relates to lighting systems for machine vision systems.

2. Description of Related Art

Machine vision systems have been in use for many years. These systems are designed to remove the human element from the manufacturing and inspection process. Many manufacturing and inspection operations are not necessarily difficult but they are boring. It is the boredom of these tasks that causes people to become unfocused during the operation, leading to defects in the product.

Vision systems traditionally have used monochrome or gray scale systems to capture the images of objects. These systems typically view the object through a video camera to determine particular attributes of the object. The system may be used to determine if a particular attribute is present or if it is properly oriented or located within a predetermined area. These systems may provide feedback during the manufacturing process or they may be used off-line as inspection devices or manufacturing aides. The feedback system may include a computer controlled feedback loop or it may be provided through human interaction. The scales of gray may be appropriate for determining some material attributes such as size, shape or color differences; however, when the degrees of differentiation between similarly colored parts is slight, a color system may be required. Thus, color recognition systems have also been incorporated into machine vision systems for more complex tasks. All of these systems rely on a sensory input device, typically a camera, a processor and a lighting device, to control the lighting of the object to be analyzed. The advent of powerful computing systems has allowed the development of the colored system. These color systems require more computations per second because of the complexity of the system. Many of these systems work on high-speed productions lines where any reduction in speed is intolerable, necessitating the need for increased computational power.

Lighting is a vital part of both the gray-scale and color systems. If the lighting does not create the proper contrast or color, the system will slow down, give false indications, or completely fail to operate. Several lighting systems are available for these vision system applications.

Vision systems typically require a light source with full visible-spectrum light emission. The light source produces light and the light is reflected off of an object to be inspected. The sensing system (e.g., camera) collects the reflected light and a processor analyzes the image for color and/or contrast. If the light source does not emit wavelengths compatible with the color of the object, the contrast between the targeted attribute and other attributes will be low. This low contrast can lead to false readings or false indications. To avoid such problems, vision systems generally use light sources that emit light throughout the visible spectrum. These light sources typically do not provide equal amounts of energy throughout the visible spectrum but they do emit some energy throughout most of the spectrum. In the case of an incandescent or halogen source, the red emission is high but the energy level is drastically reduced as the wavelength shortens, so there is very little blue emission. Fluorescent lamps tend to have gaps in the spectral output where there may be little or no emission. Once a light source is selected and the vision system is programmed, it is important that the lighting conditions remain constant. If the lighting conditions change, the reflected light and the resulting image may also change. Periodic calibrations may be provided to compensate for changing conditions within the light source.

There are several methods for analyzing the reflected light. One such method is referred to as the RGB or red, green, blue method. The RGB method involves representing all colors as a mixture of red, green and blue which constitute the primary colors used by video cameras, televisions, and PC monitors. When combined, these colors can create any color within the visible light spectrum. The second method is referred to as the HIS or hue, saturation and intensity method. HIS is based on how humans perceive color so the method is more intuitive than RGB. The method of data interpretation depends on the complexity of the task. Where coarse degrees of color separation are required, such as when identifying a red component from a green component, the RGB method may be chosen. Where the degrees of color are much finer, such as sorting pharmaceutical tablets or inspecting fruit, the HIS method may be used.

Many other methods of data interpretation and manipulation could be used or developed. Lighting is an integral part of all vision systems and it would be useful to have a lighting system incorporated into the vision system. It would also be useful to have the vision system communicate with the lighting system to create various effects.

SUMMARY OF THE INVENTION

One embodiment of the present invention is directed to a machine vision system comprising a first processor, and a lighting system capable of producing and modulating light, wherein the first processor communicates lighting command signals to the lighting system.

An embodiment of the present invention is directed to a method of lighting an object or surface in a machine vision system. The method comprises acts of providing a machine vision system, providing a lighting system capable of producing and modulating light, and communicating lighting command signals from the machine vision system to the lighting system.

Another embodiment of the present invention is directed to a method of lighting an object or surface in a machine vision system. The method comprises acts of providing a machine vision system that includes an optical system for viewing an object; providing an object; arranging the optical system to view the object; arranging a lighting system to irradiate the object, wherein the lighting system is capable of producing and modulating light; communicating first lighting control commands from the machine vision system to the lighting system; and executing a machine vision function and then having the machine vision system communicate second lighting control commands to the lighting system.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

DETAILED DESCRIPTION OF THE ILLUSTRATIVE EMBODIMENTS(S)

Figure 1:
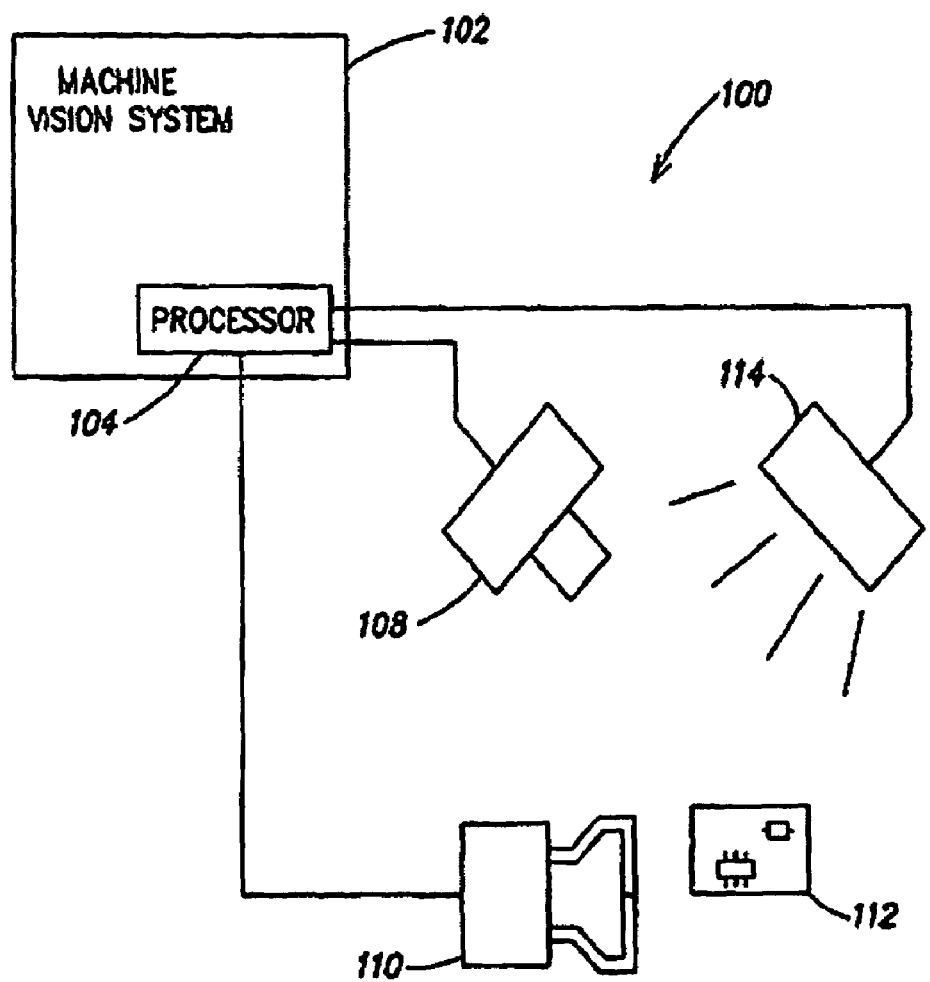
FIG. 1 illustrates a machine vision system according to one embodiment of the present invention.

The description below pertains to several illustrative embodiments of the invention. These are described merely for illustrative purposes, as the scope of the invention is not to be limited in any way by the disclosure below.

The development of high brightness LEDs and the development of digital lighting technology has created many opportunities for LED lighting. U.S. Pat. Nos. 6,016,038 and 6,211,626 describe many such lighting devices. U.S. Pat. Nos. 6,016,038 and 6,211,626 are hereby incorporated by reference herein. These patents describe methods of controlling the light output from a lighting system comprised of different colored LEDs for example. Embodiments of these patents describe the use of pulse width modulation (PWM) and independent control of the LEDs to produce varying color within a color spectrum.

In one embodiment of the present invention, an LED lighting device with color changing capabilities may be used to illuminate objects in a vision system or machine vision system. The device may be an independently controlled device with operator control or the device could be incorporated into the machine vision system. The lighting device may also be networked to other devices in the manufacturing or inspection system. As an example, an upstream process change may take place and a signal could be sent to the lighting device to change its mode of operation. If the lighting device was incorporated into the vision system, the vision system processor may control the operation of the device. A light detection unit could also be employed to constantly or periodically measure the light output from the lighting device. This information could be used to recalibrate the device for overall intensity or particular wavelengths.

A lighting device according to the principles of the present invention may include two or more different colored LEDs or it could have a single colored LED. The intensities of the respective LEDs could be varied and controlled through pulse width modulation or other LED control techniques. This system may be suited for color changing effects but it may also be used in a constant color mode. This system may be used for vision applications that require fast activation times, such as on a high-speed production line. The LED device can be turned off or the intensity reduced during the periods where the product or objects are being transferred into the vision station and be reactivated during the period of desired exposure. The LED system may also be used for providing saturated colors with high energy at wavelengths where other light sources cannot produce. With red, green and blue LEDs, the high energy can be produced in all three of these areas, as compared with halogen lamps that produce very little radiation in the blue and fluorescent lamps that have gaps in one of these areas. Any variation of hue, saturation, and intensity can be made with a combination of LEDs. The LED control signals can also be adjusted to avoid any mismatch between the video capture rate and the lighting. Another unique attribute of the LED device is that it activates so quickly that the lighting can give a strobing effect. This can be used on continuous flow systems where the strobe rate appears to freeze the objects so they can be viewed. The strobing effect is commonly used where high-speed visualization is required, however, an LED system according to the principles of the present invention can provide strobing in different colors. The rate of strobe and the rate of color change may be independent and may be controlled through the vision system or as an independent device.

Another example of the usefulness of a system according to one embodiment of the present invention is where the vision system needs to recognize several colors. The lighting effects can change as the system recognizes the attributes. If the object being viewed by the system has a blue and red wires that need to be identified, the system can activate the blue LEDs to create contrast between the blue wire and its surroundings and then perform a similar function with the red LEDs activated for the red wire. When only the blue LEDs are on, the blue wire will reflect the light and the red wire will not, enabling the blue wire to be easily identified. This is merely one simple example of an identification method that can be employed using an LED light source—many other recognition patterns are possible. This example serves to illustrate that the lighting effects can quickly and easily be changed to suit the particular application. Techniques using the principles of the present invention may also reduce the undesirable effects caused by uncontrolled changing lighting conditions. The high contrast provided by such a system may reduce or eliminate the need for calibration of the lighting system.

In one embodiment, a lighting system may also be used in conjunction with other lighting devices or filters to create other desired effects. Moving filters can be used with this system and may be desired when the filters create a desired lighting effect and the speed of the system is not as critical.

Another example of the advantages of using a device as described herein is where ultraviolet light is required to image the object or where both ultraviolet and visible or infrared are required. The vision system can be configured to receive the ultraviolet, visible and/or infrared radiation to make these lighting effects useful. The system can then activate the LEDs separately or simultaneously to provide various effects. Many objects reflect or fluoresce under ultraviolet light and thus can be easily identified through ultraviolet irradiation. These effects may be most pronounced when radiation is limited to the ultraviolet and in this case the ultraviolet radiation and identification process could take place before any visible identifications where made. Again, these lighting conditions can be changed almost instantaneously to provide fast system response.

Another method of computer vision involves creating three-dimensional shapes through the analysis of images and shadows cast on the image. The shading produced when an object is illuminated can be used effectively to recover its shape, reflection parameters, and also the direction and characteristics of the light source illuminating it. A lighting system according to the principles of the present invention may be used in such computer vision systems. The addition of color control may also aid in the reconstruction of the surface texture and color. By controlling the wavelength of radiation to more precise limits, the reflectance properties can be better approximated leading to a superior rendition of the surface properties.

FIG. 1 illustrates a machine vision system 100 according to one embodiment of the present invention. In this embodiment, the machine vision system is constructed of several elements such as a lighting system 114, a vision system (e.g., camera) 108, and an assembly apparatus 110. These elements may be considered peripherals to the central machine vision system 102. The machine vision system may include a processor 104 that controls and/or receives data from the peripherals 108, 114, and 110. The vision system 108 may be arranged to view an object 112. The object 112 may be any object, surface, or material and may be the subject of inspection or manufacture by or through the machine vision system. In another embodiment, the machine vision system 102 may not include assembly apparatus 110, because the primary objective of the system 102 may be inspection rather than assembly.

Figure 2:
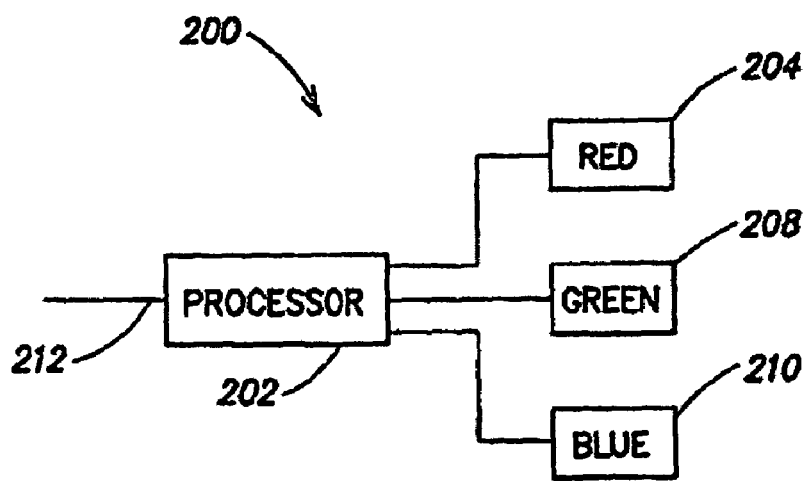
FIG. 2 illustrates a lighting system that can be used with the machine system of FIG. 1.

In one embodiment, the lighting system 114 may be associated with the processor 104 such that the processor directs commands to the lighting system 114 and the lighting system 114 responds by changing the illumination conditions in accordance with the commands. In one embodiment, the lighting system 114 is an LED lighting system 114 and the LED lighting system 114 may receive control signals from the processor 104. For example, the LED lighting system 114 may include one or more LEDs and the processor may generate and communicate control signals to the LED(s). The control signals may be pulse width modulated signals, pulse amplitude modulated signals, pulse displacement modulated signals or other modulated signals. The control signals may also be analog control signals (e.g., voltage, current, power control signals). In another embodiment, the lighting system 114 may include a second processor 202 (FIG. 2) wherein the processor 104 communicates lighting control signals to the second processor 202. The second processor 202 may receive and interpret the lighting control signals and generate lighting element control signals. For example, the processor 104 may communicate lighting control signals indicating a specific value for the hue, saturation and intensity of the light to be generated by the lighting system 114. The second processor 202 may receive the control signals and generate lighting element control signals to control the lighting element(s) of the lighting system 114. In one embodiment, the lighting system 114 may be an LED lighting system 114 wherein the LED lighting system 114 includes a second processor. As shown in FIG. 2, the LED lighting system 114 may also include several LEDs of different colors (e.g., red 204, green 208 and blue 210). The second processor may, for example, control the LEDs independently with pulse width modulated signals to change the light emitted from the lighting system 114.

In one embodiment, the lighting system 200 (FIG. 2) may be included in a lighting system 114, and includes a processor 202 and one or more LEDs 204, 208, 210. The LEDs in this example are illustrated as red 204, green 208, and blue 210, but the LEDs may be any color suitable for the user's task. The processor 202 may include a data input 212. In one embodiment, the machine vision processor 104 may communicate lighting control signals to the lighting system processor 202 through the data input 212. The communication may be accomplished through wired or wireless communication techniques.

The vision system 108 may be a color vision system or a gray scale (e.g., shade of one color) or other system. Changing the lighting conditions on the object 112 can increase the contrast between sections of the object 112 in either a color system or a gray scale system, and as a result, an intelligent lighting system 114 may be useful in either system.

In one embodiment, the lighting system 114 may be capable of producing varying degrees of color (e.g., hue, saturation and intensity) and the color may include ultraviolet spectra, infrared spectra or other spectra. In one embodiment, the lighting system may be an LED lighting system with three colors (e.g., red 204, green 208 and blue 210) and these individual or groups of LEDs may be varied in intensity. As the light from these LEDs combines, a combined color is formed (additive color mixing) and the varied intensities may cause the combined color to change. For example, the machine vision system may be viewing the object 112 through the vision system 108 wherein the processor 104 is attempting to locate a blue portion of the object 112 (e.g., a wire), so the processor 104 may communicate lighting control signals to the lighting system such that the lighting system produces blue light to increase the contrast between the blue wire and the other portions of the object 112. In one embodiment, the processor 104 may attempt to find another portion of the object 112 (e.g., a red wire) and the processor 104 may communicate lighting control signals to the lighting system 114 to change the light to red before attempting to locate the red wire to increase the contrast between the red wire and other portions of the object 112. This is just one example of how a machine vision system 102 with a controllable lighting system 114 according to the principles of the present invention can be used to increase the effectiveness of such a system, and it should be understood that such a system may be used in a variety of ways.

Figure 4:
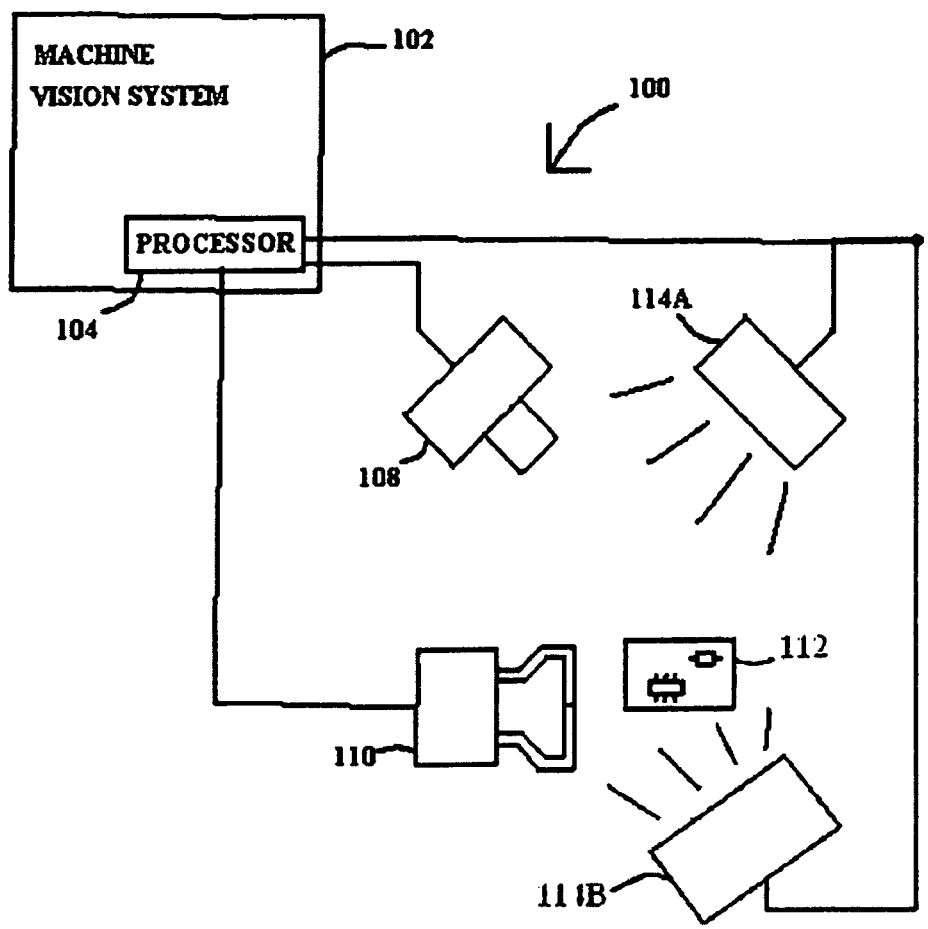
FIG. 4 illustrates a machine vision system according to another embodiment of the present invention.

In one embodiment, as shown in FIG. 4. the machine vision system 102 may be associated with more than one lighting system 114A and 114B. More than one lighting systems 114A and 114B may be used to light a same object 112, or the lighting systems 114A and 114B maybe used to light more than one object 112. For example, an object 112 may be lit with two or more lighting systems 114A and 114B to provide irradiation from different angles or for different cameras 108. The machine vision system 102 may direct lighting commands to the first lighting system such that the object is lit and the first camera identifies a portion of the object and then the machine vision system may direct a new command to the first lighting system 114A (e.g., turning it off) followed by lighting commands for the second lighting system 114B. In this arrangement, it may be useful to provide addressable processors in the lighting systems 114A and 114B such that they can read network commands to simplify the communication system. In another embodiment, it may be desirable to have direct communication from the machine vision system 102 to the lighting systems 114A and 114B.

One of the advantages of providing a lighting system 114 that is comprised of LEDs is that the LEDs can react very quickly. The LEDs can produce full output and then return to zero output within frame rates of the vision system. This means an LED lighting system 114 can change the lighting effects or illumination conditions provided to the object 112 within the time it takes the machine vision system to recognize the portion of the object 112 it is attempting to identify. This provides a machine vision system 102 that can change the illumination conditions for each operation it under takes without slowing the equipment, which can be important in some applications.

Although many of the embodiments herein describe LED lighting systems 114, in other embodiments the lighting system may be comprised of illumination sources other than LEDs. For example, the lighting system 114 may include a fluorescent, incandescent, halogen, high intensity discharge or other illumination source. In one embodiment, one of these other illumination sources may be combined with LEDs to form the lighting system 114. For example, the lighting system may be arranged with a halogen illumination source and an LED illumination source such that the machine vision system 102 can direct lighting commands to the lighting system 114 to control the halogen and LED illumination sources.

Figure 3:
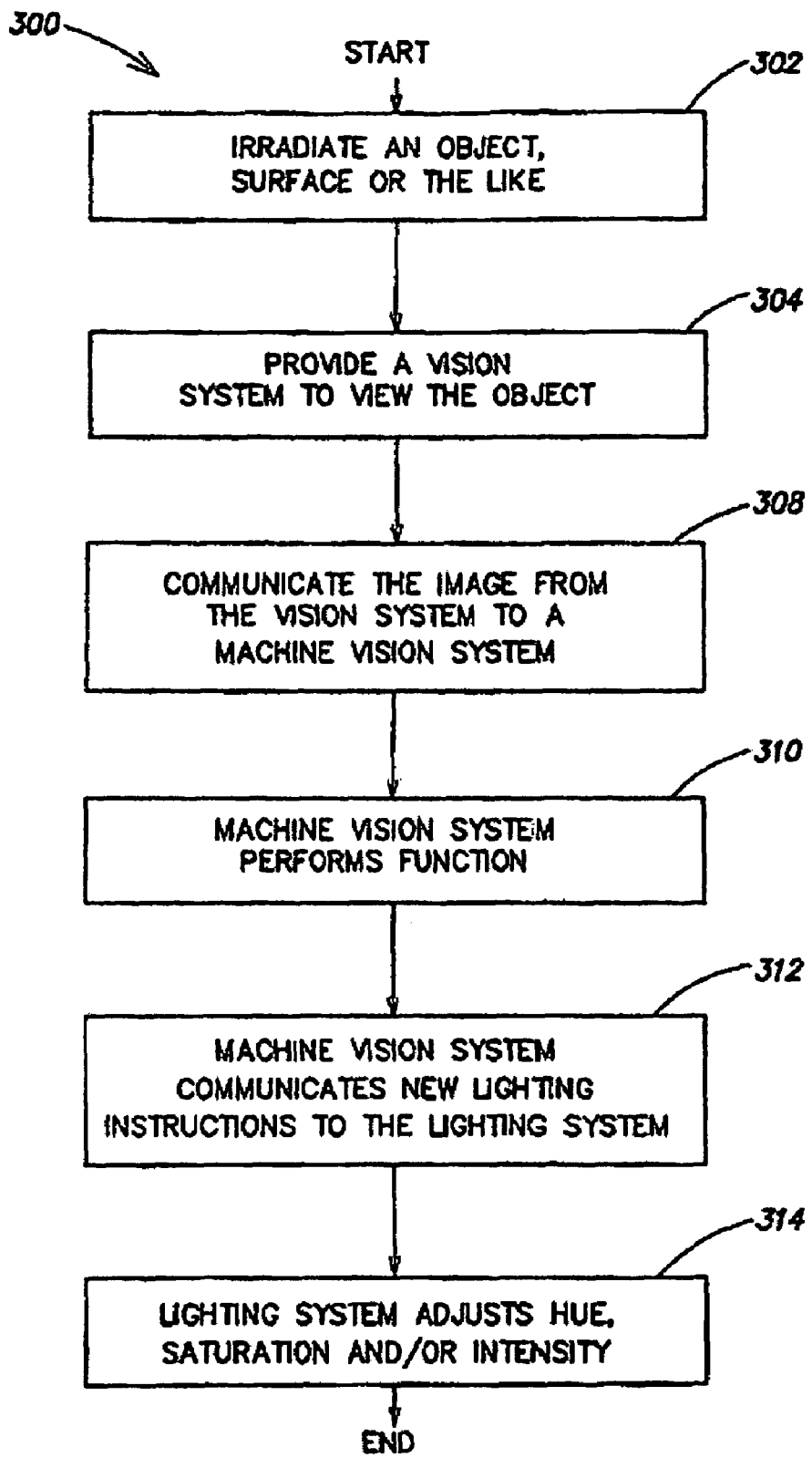
FIG. 3 illustrates a flow diagram of a lighting process for a machine vision system to one embodiment of the present invention.

FIG. 3 is a flow diagram of a process 300 according to one embodiment of the present invention. In this embodiment, the first act 302 is to irradiate an object, surface or the like with light from a lighting system. The lighting system may be capable of changing the properties of the light produced from the lighting system. A vision system may then be provided to view and capture an image of a portion of the object (act 304). The illumination conditions provided by the lighting system may be used to alter the image as viewed or captured. The image then may be communicated to a machine vision system in act 308. The machine vision system may be arranged to then perform an inspection, manipulation or other function (act 310) and then direct new lighting commands to the lighting system to change the illumination conditions provided to the object (act 312). In response to the lighting commands, the lighting system may then change the hue, saturation and/or intensity of the light produced by the lighting system (act 314) to provide new lighting conditions for the next portion of the object to be identified. While this process can be implemented in numerous ways, in an embodiment the process is executed on a processor (e.g., 104 in FIG. 1) in the machine vision system.

As used herein, the term "LED" should be understood to include light emitting diodes of all types, light emitting polymers, semiconductor dies that produce light in response to current, organic LEDs, electro-luminescent strips, and other such systems. An "LED" may refer to a single light emitting diode having multiple semiconductor dies that are individually controlled. It should also be understood that the term "LED" does not restrict the package type of the LED. The term "LED" includes packaged LEDs, non-packaged LEDs, surface mount LEDs, chip on board LEDs and LEDs of all other configurations. The term "LED" also includes LEDs packaged or associated with material (e.g., a phosphor) wherein the material may convert energy from the LED to a different wavelength.

The term "illuminate" should be understood to refer to the production of a frequency of radiation by an illumination source. The term "color" should be understood to refer to any frequency of radiation within a spectrum; that is, a "color," as used herein, should be understood to encompass frequencies not only of the visible spectrum, but also frequencies in the infrared and ultraviolet areas of the spectrum, and in other areas of the electromagnetic spectrum.

Having described several embodiments of the invention in detail, various modifications and improvements will readily occur to those skilled in the art. Such modifications and improvements are intended to be within the spirit and scope of the invention. Accordingly, the foregoing description is provided by way of example only, and is not intended to be limiting. The invention is limited only as defined by the following claims and the equivalents thereto.

What is claimed is:

1. A method of illuminating an object, for use with a machine vision system comprising A) a first lighting system adapted to produce light, the first lighting system comprising i) a first light source adapted to produce a first light component having a first spectrum, ii) a second light source adapted to produce a second light component having a second spectrum, the first spectrum being different than the second spectrum, and iii) a first processor, and B) a second processor, the method comprising:

illuminating the object with the first light component;
illuminating an object with the second light component;
transmitting a first lighting command signal from the second processor to the first processor; and
modulating at least one of the first light and the second light with the first processor, in accordance with the first lighting command signal.

2. A machine vision system, comprising:

A) an addressable first lighting system adapted to produce light, the addressable first lighting system comprising:
   i) a first light source adapted to produce a first component of the light having a first spectrum; and
   ii) a second light source adapted to produce a second component of the light having a second spectrum, the first spectrum being different than the second spectrum; and
B) a processor coupled to the addressable first lighting system and adapted to transmit first lighting command signals to modulate the light, the addressable first lighting system being configured to distinguish the first lighting command signals from other information transmitted by the processor.

3. The machine vision system of claim 2, wherein at least one of the first light source and the second light source comprises at least one LED.

4. The machine vision system of claim 2, wherein the processor is configured to modulate at least one of the first light source and the second light source to change at least one of a hue, a saturation and an intensity of the light.

5. The machine vision system of claim 2, wherein at least one of the first light source and the second light source comprises a UV radiation source.

6. The machine vision system of claim 2, wherein the first lighting command signals are selected to achieve at least one of pulse width modulation, pulse amplitude modulation, and pulse displacement modulation of at least one of the first light source and the second light source.

7. The machine vision system of claim 2, further comprising a vision system.

8. The machine vision system of claim 7, wherein the vision system is adapted to produce a gray scale image of an object illuminated by the light.

9. The machine vision system of claim 2, further comprising a second lighting system adapted to produce a second light, wherein the first lighting system is adapted to illuminate an object at a first illumination angle and the second illumination system is adapted to illuminate the object at a second illumination angle.

10. The machine vision system of claim 9, wherein the second lighting system comprises:

i) a third light source adapted to produce a first component of the second light having a third spectrum; and ii) a fourth light source adapted to produce a second component of the second light having a fourth spectrum, the third spectrum being different than the fourth spectrum.

11. The machine vision system of claim 9, wherein the processor is coupled to the second lighting system and adapted to transmit second lighting command signals to modulate the second light.

12. A method of illuminating an object, for use with a machine vision system, the method comprising steps of:
   in accordance with at least one first addressed command signal, illuminating the object with a first light having a first spectrum and a second light having a second spectrum, the first spectrum being different than the second spectrum; and
   modulating at least one of the first light and the second light, whereby the object is illuminated with modulated light.

13. The method of claim 12, wherein at least one of the first light and the second light comprises light from an LED.

14. The method of claim 12, wherein the step of modulating comprises modulating at least one of the first light and the second light to change at least one of a hue, a saturation and an intensity of light incident on the object.

15. The method of claim 12, wherein at least one of the first light and the second light comprises UV radiation.

16. The method of claim 12, wherein the step of modulating comprises at least one of pulse width modulating, pulse amplitude modulating, and pulse displacement modulating at least one of the first light and the second light.

17. The method of claim 12, further comprising a step of forming an image of the object with at least one of a portion of the first light and a portion of the second light.

18. The method of claim 17, wherein the image is a gray scale image.

19. The method of claim 12, wherein the first light illuminates the object at a substantially same angle as the second light.

20. The method of claim 19, further comprising a step of illuminating the object at a second illumination angle with a third light.

21. The method of claim 20, further comprising a step of illuminating the object with a fourth light at the second illumination angle, the fourth light having a fourth spectrum that is different than the third spectrum.

22. The method of claim 21, further comprising modulating at least one of the third light and the fourth light.

23. A machine vision system, comprising:
   a first lighting system adapted to produce light in response to at least one lighting command signal, the first lighting system comprising:
   i) a first light source adapted to produce a first light component having a first spectrum; and
   ii) a second light source adapted to produce a second light component having a second spectrum, the first spectrum being different than the second spectrum; and
   iii) a processor adapted to receive the at least one lighting command signal and modulate at least one of the first light component and the second light component in accordance with the at least one lighting command signal.

24. The machine vision system of claim 23, wherein at least one of the first light source and the second light source comprises at least one LED.

25. The machine vision system of claim 23, wherein the processor is configured to modulate at least one of the first light source and the second light source to change at least one of a hue, a saturation and an intensity of the light.

26. The machine vision system of claim 23, wherein at least one of the first light source and the second light source is a UV radiation source.

27. The machine vision system of claim 23, wherein the at least one lighting command signal is adapted to achieve at least one of pulse width modulation, pulse amplitude modulation, and pulse displacement modulation of at least one of the first light source and the second light source.

28. The machine vision system of claim 23, further comprising a vision system.

29. The machine vision system of claim 28, wherein the vision system is adapted to produce a gray scale image of an object illuminated by the light.

30. The machine vision system of claim 23, further comprising a second lighting system adapted to produce a second light, wherein the first lighting system is adapted to illuminate an object at a first illumination angle and the second illumination system is adapted to illuminate the object at a second illumination angle.

31. The machine vision system of claim 30, wherein the second lighting system comprises:
   i) a third light source adapted to produce a first component of the second light having a third spectrum; and
   ii) a fourth light source adapted to produce a second component of the second light having a fourth spectrum, the third spectrum being different than the fourth spectrum.

32. The machine vision system of claim 30, wherein the second lighting system comprises a second processor adapted to receive at least one second lighting command signal to modulate the second light.

33. A machine vision system, comprising:
   A) a first lighting system adapted to produce light, the first lighting system comprising:
   i) a first light source adapted to produce a first light component of the light having a first spectrum;
   ii) a second light source adapted to produce a second light component of the light having a second spectrum, the first spectrum being different than the second spectrum; and
   iii) a first processor adapted to receive a first lighting command signal to modulate the light; and
   B) a second processor coupled to the first lighting system and adapted to transmit the first lighting command signal to the first processor.

34. A machine vision system of claim 33, wherein the first lighting system is an addressable lighting system.

* * * * *